United States Patent [19]
Costa

[11] Patent Number: 6,063,065
[45] Date of Patent: May 16, 2000

[54] PREPACKAGED ABSORBENT ARTICLE WITH PARTIALLY NON-COEXTENSIVE WRAPPER

[75] Inventor: Rogerio Costa, Lorena-SP, Brazil

[73] Assignee: Johnson & Johnson Industria E. Comercio LTDA, Brazil

[21] Appl. No.: 09/093,550

[22] Filed: Jun. 8, 1998

[51] Int. Cl.[7] .............................. A61F 13/15; A61B 17/06
[52] U.S. Cl. ...................... 604/385.1; 604/393; 604/387; 206/438
[58] Field of Search ................................. 604/385.1, 393, 604/387; 206/438

[56] References Cited

U.S. PATENT DOCUMENTS

| | | |
|---|---|---|
| H1363 | 10/1994 | Leeker . |
| H1454 | 6/1995 | Cucuzza et al. . |
| 1,352,962 | 9/1920 | Hitzigrath . |
| 1,630,343 | 5/1927 | Hurlbut . |
| 2,449,334 | 9/1948 | Smith . |
| 2,750,033 | 6/1956 | Pickens . |
| 3,035,578 | 5/1962 | Elmore . |
| 3,062,371 | 11/1962 | Patience . |
| 3,193,181 | 7/1965 | Konjevich et al. . |
| 3,561,593 | 2/1971 | Ruda . |
| 3,698,549 | 10/1972 | Glassman . |
| 3,877,432 | 4/1975 | Gellert . |
| 3,963,029 | 6/1976 | Brooks . |
| 3,973,567 | 8/1976 | Srinivasan et al. . |
| 4,286,639 | 9/1981 | Murphy . |
| 4,402,689 | 9/1983 | Baum . |
| 4,551,145 | 11/1985 | Ryan . |
| 4,556,146 | 12/1985 | Swanson et al. . |
| 4,607,633 | 8/1986 | Lauritzen . |
| 4,648,513 | 3/1987 | Newman . |
| 4,692,162 | 9/1987 | Binker et al. . |
| 4,735,316 | 4/1988 | Froidh et al. . |
| 4,765,477 | 8/1988 | Froidh et al. . |
| 4,781,712 | 11/1988 | Barabino et al. . |
| 4,917,675 | 4/1990 | Taylor et al. . |
| 5,088,993 | 2/1992 | Gaur . |
| 5,181,610 | 1/1993 | Quick et al. . |
| 5,295,988 | 3/1994 | Muckenfuhs et al. . |
| 5,380,094 | 1/1995 | Schmidt et al. . |
| 5,413,568 | 5/1995 | Roach et al. . |
| 5,462,166 | 10/1995 | Minton et al. . |
| 5,478,336 | 12/1995 | Pigneul . |
| 5,484,636 | 1/1996 | Berg et al. . |
| 5,569,228 | 10/1996 | Byrd et al. . |
| 5,569,230 | 10/1996 | Fisher et al. . |
| 5,683,377 | 11/1997 | Mizutani . |

FOREIGN PATENT DOCUMENTS

| | | |
|---|---|---|
| 2 221 667 | 2/1990 | United Kingdom . |
| 88/10219 | 12/1988 | WIPO . |
| WO 91/16873 | 11/1991 | WIPO . |
| 91/18574 | 12/1991 | WIPO . |
| 93/21878 | 11/1993 | WIPO . |
| 94/04111 | 3/1994 | WIPO . |
| 94/16659 | 4/1994 | WIPO . |
| 94/14396 | 7/1994 | WIPO . |
| 95.93923 | 2/1995 | WIPO . |
| WO 97/16143 | 5/1997 | WIPO . |
| 98/53781 | 3/1998 | WIPO . |
| 98/53782 | 3/1998 | WIPO . |

*Primary Examiner*—John G. Weiss
*Assistant Examiner*—Paul Shanoski

[57] ABSTRACT

The invention refers to a prewrapped good, notably a prewrapped sanitary napkin, which requires less handling to open and apply to the user's underwear, allowing for less hand contact and therefore greater hygiene.

15 Claims, 9 Drawing Sheets

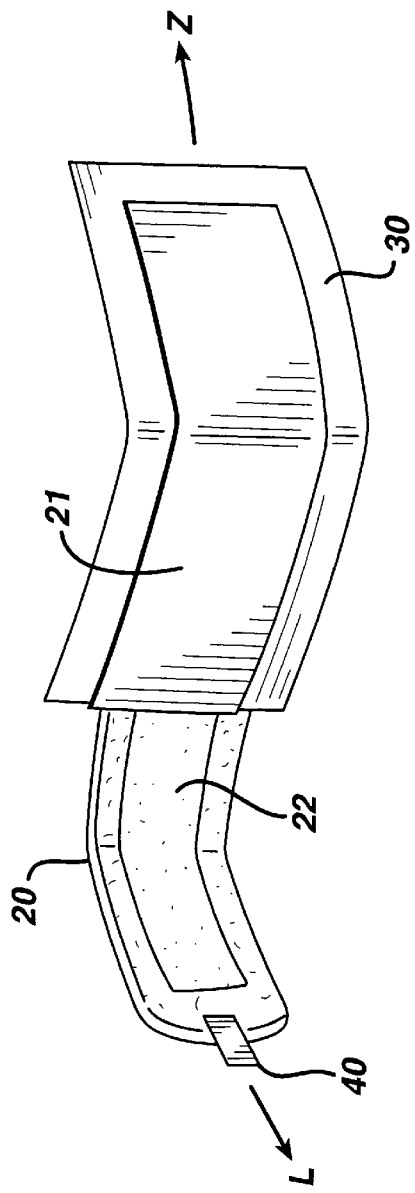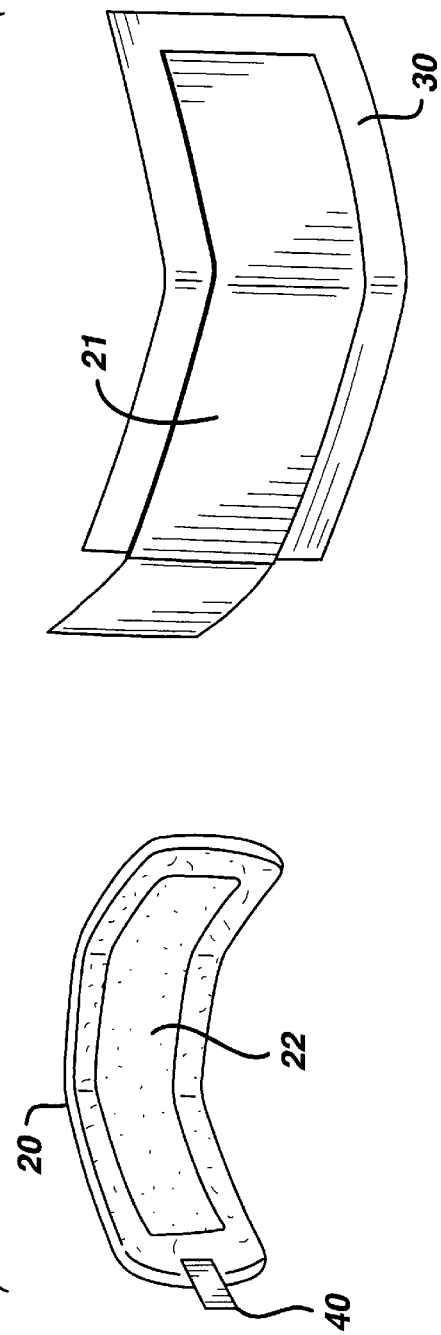

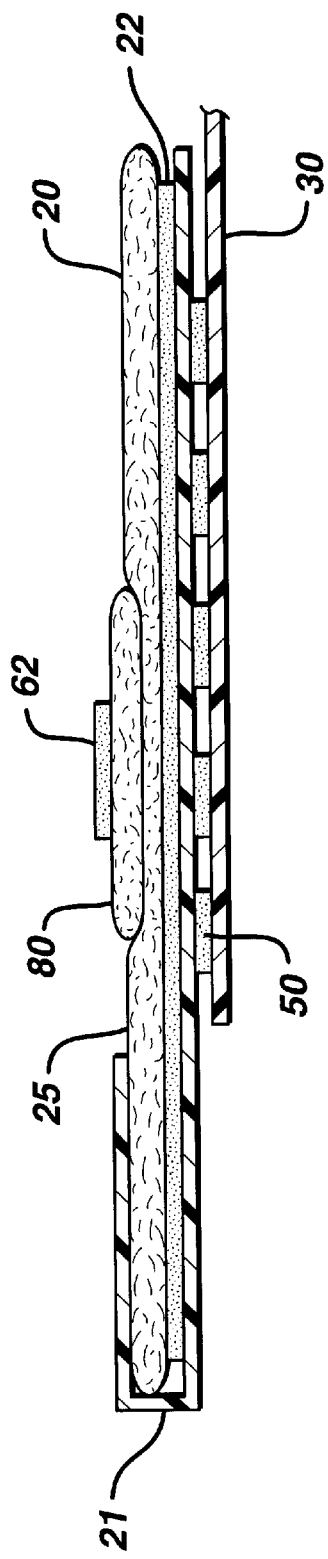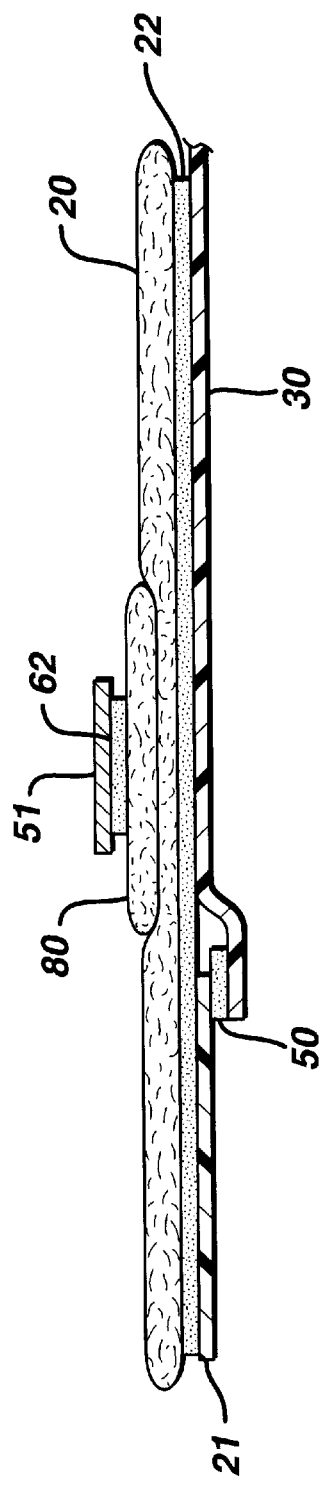

PREPACKAGED ABSORBENT ARTICLE WITH PARTIALLY NON-COEXTENSIVE WRAPPER

BACKGROUND OF THE INVENTION

The present invention provides a prepackaged good which can be opened of a package, making available a product which minimizes the amount of handling to open the package, separate the good from its wrapper, and use the good immediately after opening.

The present invention is appropriate for any type of good which is packaged, being especially useful for goods that are flexible, elongated and flat. The present invention is particularly advantageous for packaging disposable products, such as sanitary napkins for women, surgical bandages or compresses or those for home use, diapers for urinary incontinence and other similar products.

With the aim of providing greater comfort to the women who use this product, sanitary napkins have been packaged individually so they can be carried conveniently, in small numbers, for example, on a trip during pre-menstrual days or for a social event, or any other situation where it would not be desirable to carry a larger package with more units. These are products which are practical and convenient to use, as they can be carried discretely by the user, preserving their hygiene and occupying little space, in a purse, for example.

For example, U.S. Pat. No. 4,556,146 discloses an individually packaged disposable absorbent article having the absorbent pad and wrapper being folded as a unit about at least two fold axis and the absorbent article's backsheet being releasably affixed to the backsheet portion of the wrapper.

However, in order to use the individually prewrapped sanitary napkins, it is necessary to carry out several activities such as pulling, ripping, separating the napkin from the wrapper, handling the front and the back of the napkin. In view of the desire to reduce the amount of handling required, there is a long standing need for a prewrapped sanitary napkin, providing greater ease of use, less handling before it is put to use and, and as a result greater hygiene.

SUMMARY OF THE INVENTION

According to the present invention the disposable article is manufactured according to the processes known in the art. The disposable article is then packaged into a wrapper. More specifically, in a first embodiment, the present invention provides a disposable article comprising:

a pad having opposing top and bottom surfaces said pad having a distal and proximal ends, and first and second longitudinal edges extending therebetween;

a wrapper having opposing top and bottom surfaces, said wrapper having distal and proximal ends and first and second longitudinal edges extending therebetween, said longitudinal edges of said wrapper are shorter than said longitudinal edges of said pad, said top surface of said wrapper coextensive with greater than about half, but less than all bottom surface of said pad such that said longitudinal edges of said wrapper extends beyond said longitudinal edges of said pad.

In preferred embodiments the present invention provides: that the distal end of the pad is folded at least once, substantially 180 degrees toward said top surface of said pad along a first fold axis substantially perpendicular to said longitudinal edges of said pad, said first fold axis is proximal to the distal end of said wrapper; and more preferably wherein the pad and wrapper are folded substantially 180 degrees towards said top surface of said pad along a second fold axis, substantially parallel to the first fold axis, the second fold axis is proximal to said first fold axis. The present invention also provides a method for manufacturing the prewrapped absorbent article comprising:

BRIEF DESCRIPTION OF THE DRAWINGS

FIG. 1 depicts a sanitary napkin in various stages of being folded into the wrapper.

FIGS. 5 and 6 depict the opening of the napkin from the wrapper. FIGS. 7A and B, and 8 depict perspective views of various release liner configurations.

DETAILED DESCRIPTION OF THE INVENTION

The description of the present invention will use the term sanitary napkin, however, this description is not meant to limit the present invention, which includes prepackaged absorbent articles such as pantyliners, incontinence articles, catamenial pads, bandages and the like. These articles generally have a length greater than its width and have longitudinal edges which are provided along the length of the article. The opposite edges, or the transverse edges, are shorter in dimension than the longitudinal edges. The sanitary napkin although elongated, may have varied forms, such as a rectangle, quadrilateral, quadrangle, a hourglass, or any of the numerous shapes and dimensions known in the art.

The sanitary napkins are relatively thin articles, no thicker than about 5 centimeters, which have a bodyfacing surface, which is fluid permeable and a garment facing surface which is fluid impermeable. The bodyfacing surface is generally comprised of a soft cover and the garment facing surface or backsheet is typically fluid impermeable and has an adhesive in order to attach the sanitary napkin to the user's undergarment. The sanitary napkin and the wrapper have their longitudinal dimensions aligned, that is, their longitudinal edges are substantially going in the same direction. The wrapper is sealed by means known in the art, such as perforations, adhesives, frangible seals and hook and loop fasteners and the like. The sanitary napkin and the wrapper are folded in such a way that the wrapper contains the sanitary napkin and the wrapper is partially or totally sealed around its circumference.

Before being folded, the sanitary napkin is placed on the wrapper. A portion of the sanitary napkin that is not in contact with the wrapper is folded on at least one axis without the wrapper. The present invention has the non-coextexsive portion of the sanitary napkin folded onto the portion of napkin that is coextensive with the wrapper. At least one fold axis on the noncoextensive portion of the napkin must be on wrapper, typically proximal to the distal end of the wrapper. A second fold axis is formed with the sanitary napkin and wrapper one or more times as necessary or as desired. It is preferred that the wrapper and the internal body of the sanitary napkin are folded as a unit once. Since the wrapper is longer and wider than the sanitary napkin, this geometry provides for easy sealing of the wrapper, with the sanitary napkin enclosed.

Figure 1A:
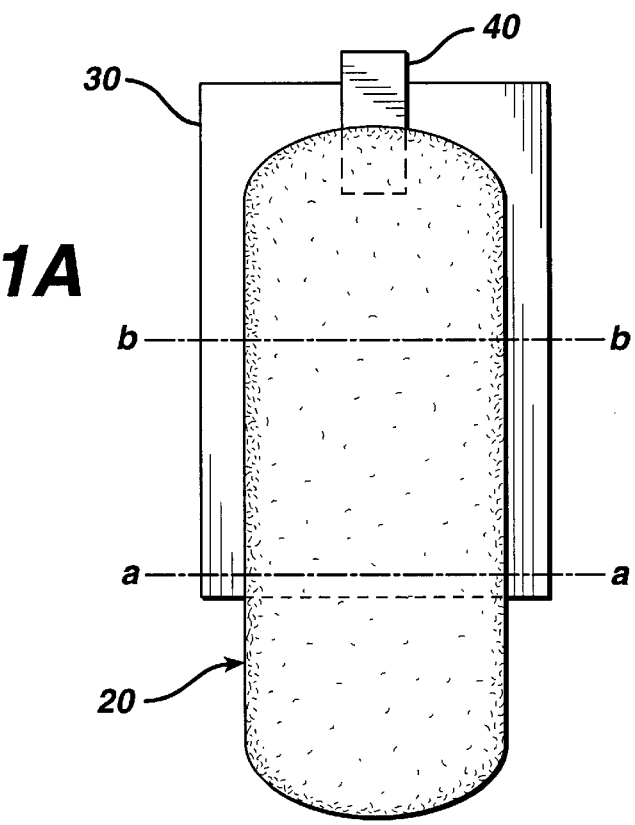
FIG. 1A depicts the napkin before being wrapped.
Figure 1B:
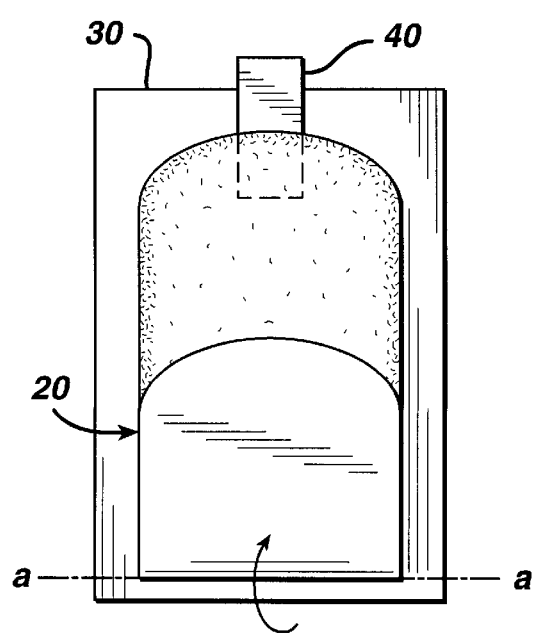
FIG. 1B depicts the napkin having one fold axis and FIG. 1C depicts the napkin as folded into and enclosed by the wrapper.
Figure 1C:
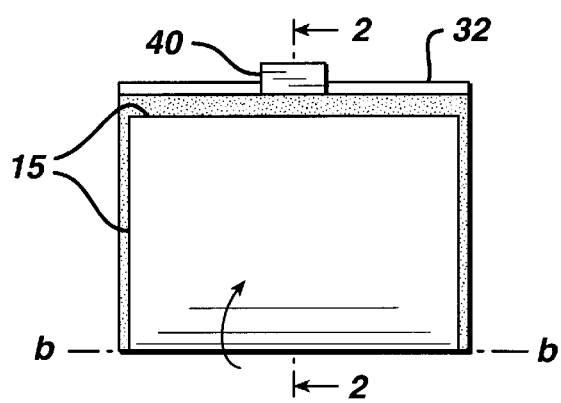

The following is a detailed description of the invention depicted in the Figures. As shown in FIG. 1A, a sanitary napkin 20 is positioned on a wrapper 30. The napkin is positioned such that at least one end is not coextensive with the wrapper. The napkin preferably has a tab 40 that extends beyond the wrapper. Greater than about 50 percent of the longitudinal (length) portion of the sanitary napkin is coextensive with the wrapper. Preferably more than 60% of the sanitary napkin is coextensive with the wrapper, most preferably greater than about 66% of the sanitary napkin is coextensive with the wrapper. In FIG. 1B the sanitary napkin is depicted having been folded one time such that the folded axis is in contact with the wrapper. The sanitary napkin is folded such that the non-coextensive portion is folded once along axis a—a such that only the sanitary napkin is folded along this axis. In FIG. 1C the wrapper and the sanitary napkin together are folded along axis b—b to provide the folded article. Along the second fold axis, b—b, the sanitary napkin and the wrapper are folded as a unit. The wrapper 30 totally contains the sanitary napkin 20, and this isolates it from the outside, as it is sealed peripherally in all areas 15. The wrapper 30 has transverse edge 32 which can be pulled by the user in the direction opposite to tab 40.

Figure 2:
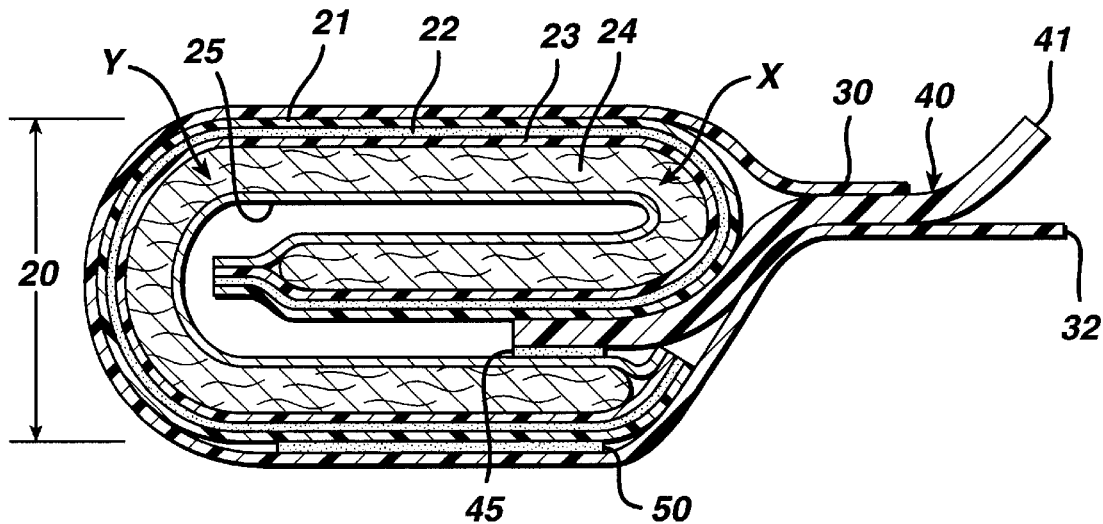
FIG. 2 is a cross-section of the prewrapped napkin in FIG. 1, depicted through axis 2—2.

The cross-sectional of structure of the sanitary napkin 20, is shown in greater detail in FIG. 2, comprising: a covering, a fluid permeable topsheet 25, which when in use comes into contact with the user's body, an absorbent material 24; and a backsheet portion 23, typically made from liquid impermeable material such as plastic film; a layer of adhesive 22, which during use, after the wrapper has been open, will fix the sanitary napkin onto the user's underwear; a release liner 21 to protect the adhesive layer 22, while the wrapper is unopened.

Tab 40 is fixed to the covering 25 in such a way that it cannot come loose with adhesive 45. Tab 40 has a part in its internal extension affixed to the sanitary napkin 20, another part to the absorbent article, so that its extremity 41 can be reached by the user's hand during opening. The release liner 21 is securely attached to wrapper 30, by the adhesive 50.

The napkin 20 is folded over itself twice, by fold areas X and Y. Contrary to the disclosure of the prior art, the absorbent article is not coextensive with the wrapper. Therefore, while the absorbent article is folded twice, the wrapper and the article are fold as a unit, a single time. This reduces the amount of wrapper paper that is required as well as making it easier to remove the sanitary napkin from the wrapper. In a highly preferred embodiment of the invention, the sanitary napkin can be removed from the package and placed in the user's undergarment without touching the sanitary napkin itself. Only the tab 40 would need to be handled. Also unlike the disclosures of the prior art, the tab is preferably adhered to the sanitary napkin rather than to the wrapper. The user, with the thumb and forefinger of one hand holds the accessible part of the tab, while with the thumb and forefinger of the other hand, the user holds the transverse edge of the wrapper. In a single motion, the user pulls the sanitary napkin and the wrapper in opposite directions, the wrapper is opened, and the sanitary napkin is separated from the wrapper. The adhesive strip used to fix the napkin to the wrapper before use is the same that remains on the back of the napkin after the wrapper has been opened. Thus, after opening, while one of the hands holds the tab of the transverse edge of the sanitary napkin, the other hand (which has already disposed of the wrapper) holds the napkin by the transversal border opposite the tab, and the user secures the napkin to her undergarment, without having to touch the sanitary napkin surface which will be in contact with her body.

Figure 2A:
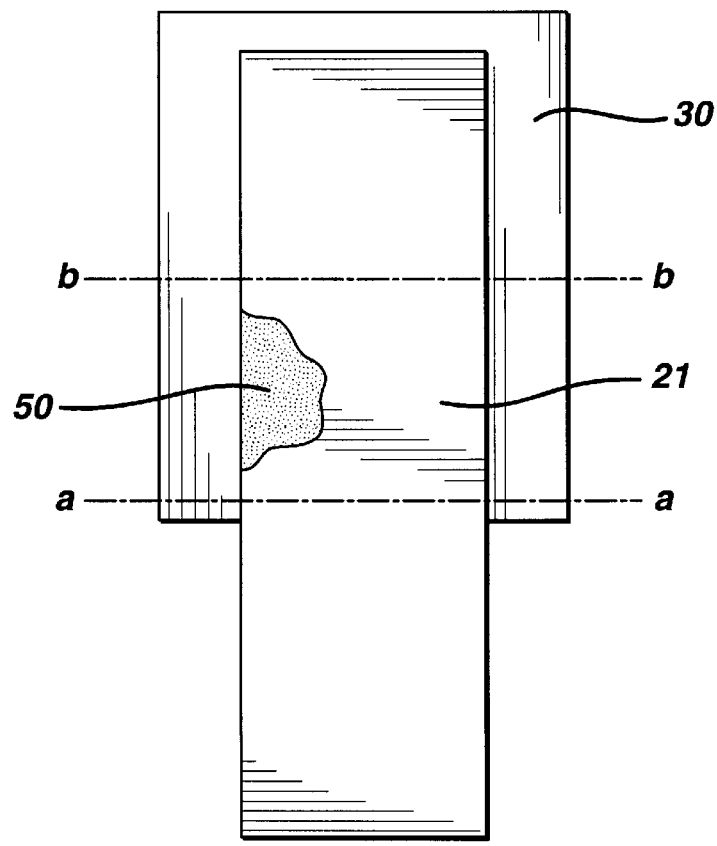
FIG. 2A depicts sanitary wrapper and the optional release liner.

FIG. 2A depicts the arrangement of the wrapper 30, release liner 21 and the adhesive 50 used to adhere the two elements to one another. The release liner is employed in a preferred embodiment of the invention. Like the sanitary napkin, most of the release liner is coextensive and preferably attached to the wrapper. In a highly preferred embodiment, the release liner is as long if not longer than the sanitary napkin. The fold line axes, a—a and b—b, are depicted as in FIG. 1.

Figure 3A:
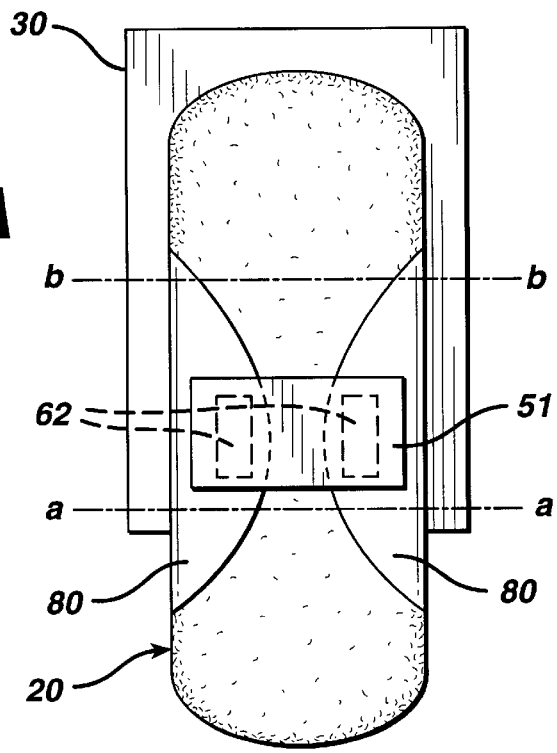
FIGS. 3, A–C and 4 A–C depict the folding sequence of a napkin with wings.
Figure 3B:
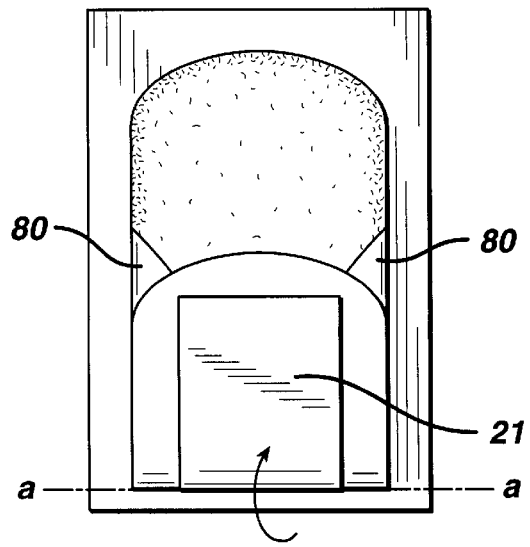
Figure 3C:
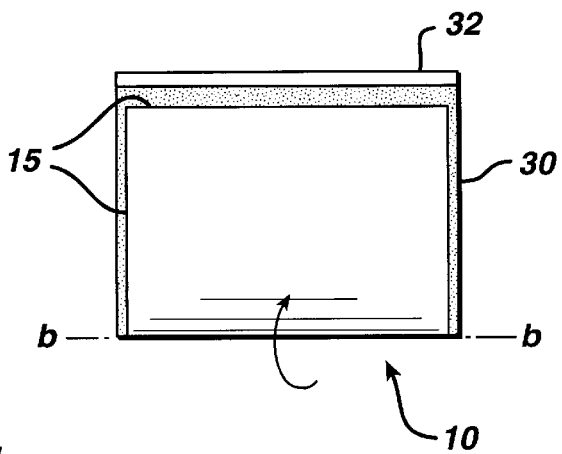

FIGS. 3A–C depict the folding arrangement of the prewrapped good 10 in which a portion of the sanitary napkin is folded over the wing. In FIG. 3A the sanitary napkin 20, which is coextensive with the wrapper is depicted with wings 80. On the wings are wing positioning adhesive 62 and a release liner 51 to protect the wing positioning adhesive prior to use. The fold axes are depicted as a—a and b—b. In FIG. 3B, the portion of the sanitary napkin section which is not coextensive with the wing is folded along axis a—a, and substantially covers the wings 80 and the release liner covering the wings. The release liner 21 protecting the sanitary napkin positioning adhesive 63 is also depicted. In FIG. 3C the wrapper and the sanitary napkin is folded along the second fold axis, b—b, simultaneously to form the pre-packaged good 10. In FIG. 3C, after being folded along axis b—b, the prepackaged good is sealed along 15, typically by heat sealing, perforations or an adhesive. The transverse edge of the wrapper 32 is also preferably sealed.

Figure 4A:
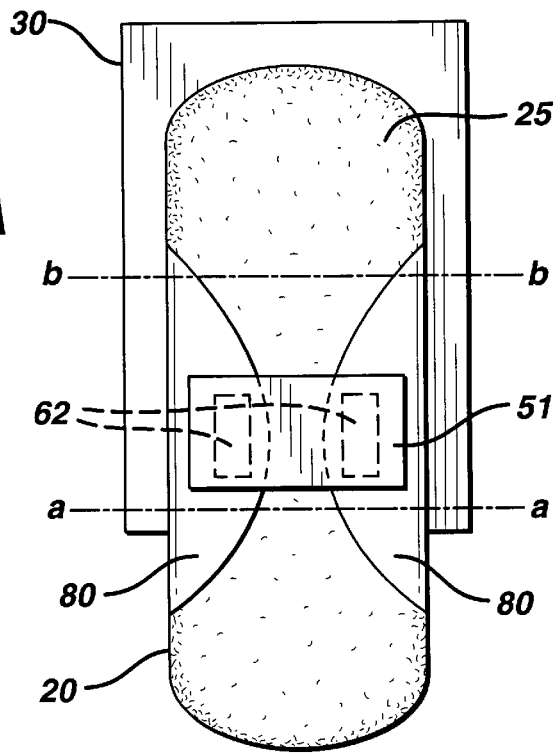
Figure 4B:
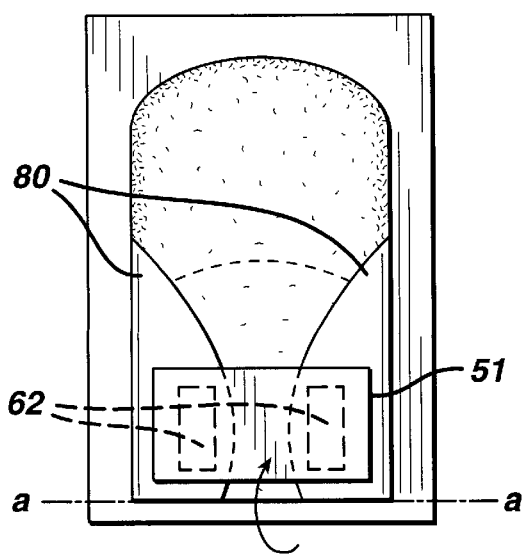
Figure 4C:
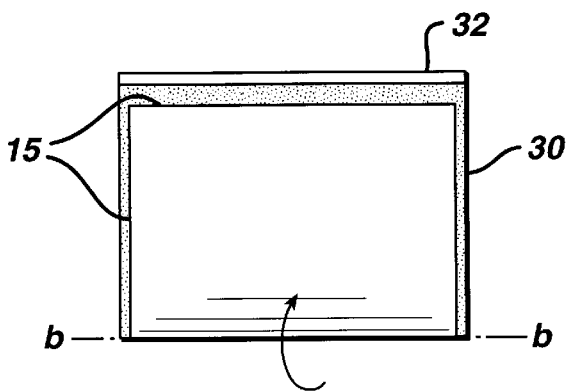

FIGS. 4A–C demonstrate an alternative folding arrangement in which the wings 80 are folded over the first folded portion of the sanitary napkin. In this arrangement, as depicted in FIG. 4B, the portion of the sanitary napkin 20 not coextensive with the wrapper 30 is folded first along axis a—a. The wings are then folded over the portion of the folded portion of the napkin and is depicted by the dashed line. The release liner 51 is placed to protect the wing positioning adhesive 62. In FIG. 4C the prewrapped article is then completed by providing the final fold along axis b—b. The package is then sealed along the edges 15 and the transverse edge 32.

FIG. 5 is an illustration of the opening sequence of the prewrapped article. The tab 40 is pulled resulting in the mechanical separation of the sanitary napkin from the wrapper. In FIG. 5 the sanitary napkin is being pulled in the L direction and the wrapper, in the opposite direction, the Z direction. The napkin positioning adhesive 22 on the sanitary napkin 20 is protected by the release liner 21, which in a highly preferred embodiment is securely attached to the wrapper FIG. 6 illustrates the sanitary napkin 20 entirely separated from the wrapper 30. The release liner 21 remains attached to the wrapper and the sanitary napkin is ready to be inserted into the user's undergarment through the manipulation of the tab 40 and the use of the napkin positioning adhesive 22.

FIG. 7A is a side view of the sanitary napkin having an alternative release liner design configuration, In this embodiment of the invention the release liner 21 extends beyond the end of the sanitary napkin and wraps around the transverse edge of the sanitary napkin 20 onto the body facing surface 25. The wings 80 and wing positioning adhesive 62 are protected by the release liner when the sanitary napkin is folded. In this embodiment the release liner that is present on the garment facing side of the sanitary napkin protects the wing position adhesive found on the wing. The adhesive 50 used to adhere release liner 21 to the wrapper 30 is depicted.

FIG. 7B depicts an embodiment of the present invention in which the amount of release liner is minimized. Only a small portion of the release liner 21 is present in order to protect the sanitary napkin 20 that is non-coextensive with the wrapper 30. The napkin positioning adhesive 22, wings 80, wings positioning adhesive 62 and the wing positioning adhesive release liner 51 are also depicted.

In a highly preferred embodiment the release liner on the wing and the release liner on the substantially coextensive piece are connected by a connecting piece (not shown). This connective piece can be a string, thread, small piece of release liner, cloth, fabric and the like. The purpose of the connecting piece is to provide for the separation of the release liners from the sanitary napkin in a single motion. In the absence of a connecting piece, the release liners would need to be removed in two separate steps.

Figure 8:
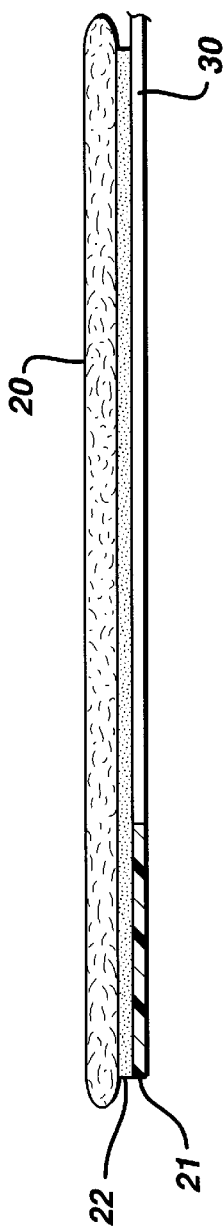

FIG. 8 depicts a side view of a sanitary napkin without wings which minimizes the amount of release liner 21 that is required. Only a small piece of the release liner is provided on the sanitary napkin which is non-coextensive with the wrapper. The release liner is adjacent to the wrapper 30. When the sanitary napkin 20 is folded over, release liner 21 prevents the positioning adhesive 22 which holds the sanitary napkin to the user's underwear, from becoming soiled and or stuck to the sanitary napkin or wrapper. The wrapper is preferably coated with a release agent, such as silicone oil thereby obviating the need for an additional release liner on the coextensive portion of the sanitary napkin with the wrapper.

Figure 9:
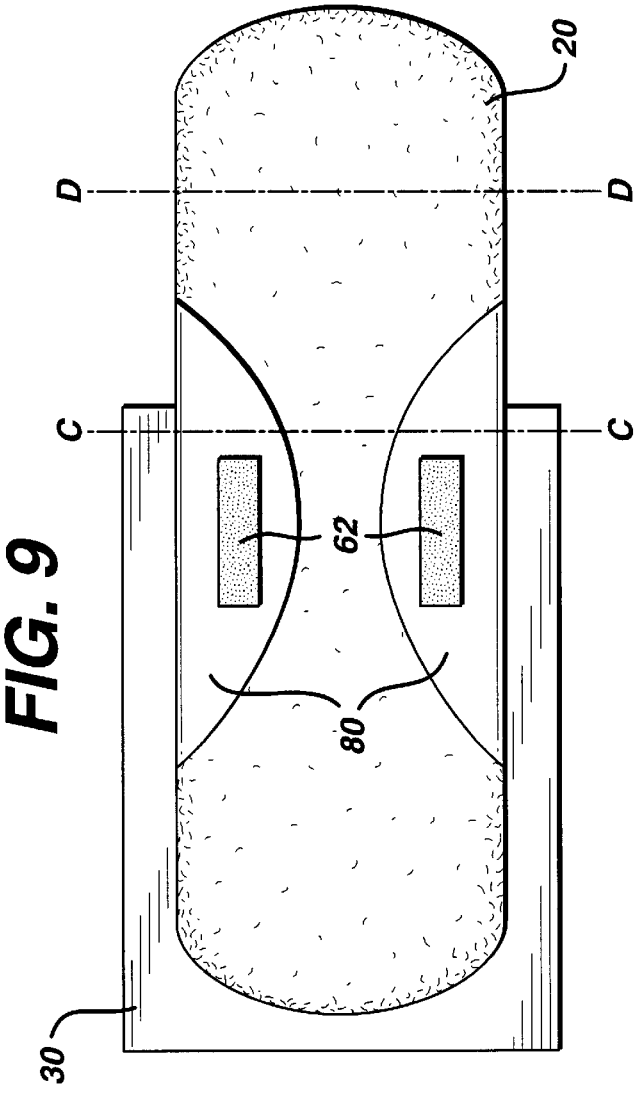
FIG. 9 depicts an alternative embodiment of the invention in which multiple fold axes are made on the non-coextensive portion to the wrapper of a sanitary napkin.

FIG. 9 is a top view looking onto the sanitary napkin 20 on the wrapper 30. In this embodiment the release liner is on the back of the sanitary napkin (not shown). In this embodiment, the portion of the sanitary napkin which is not coextensive with the wrapper is folded twice, once on axis D—D, and again on axis C—C. This arrangement eliminates the need for a separate release liner to be positioned over the wing positioning adhesive 62 found on the wings 80.

Figure 10:
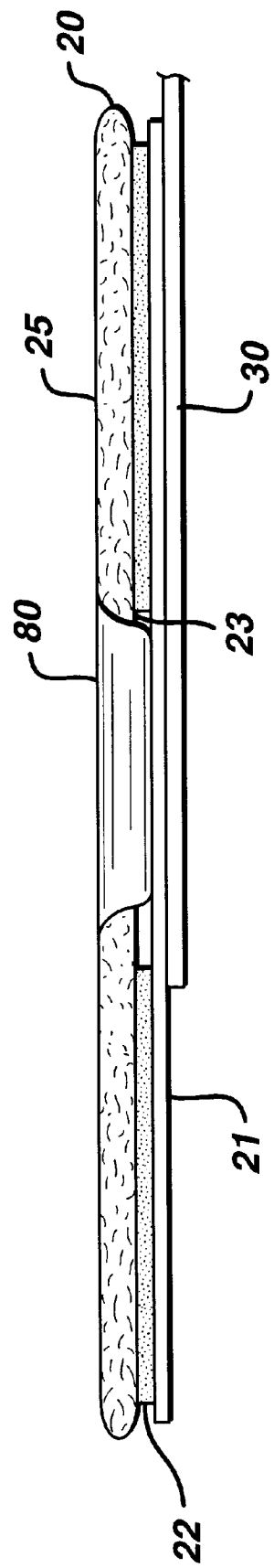
FIG. 10 depicts a napkin with a backfolded wing.

In FIG. 10, the wings 80 are backfolded, i.e., folded under the sanitary napkin 20 rather than over it. The backfolded wing is contacting the barrier layer 23 of the napkin 20. The release liner 21 protecting the napkin position adhesive 22 is also depicted.

Figure 11:
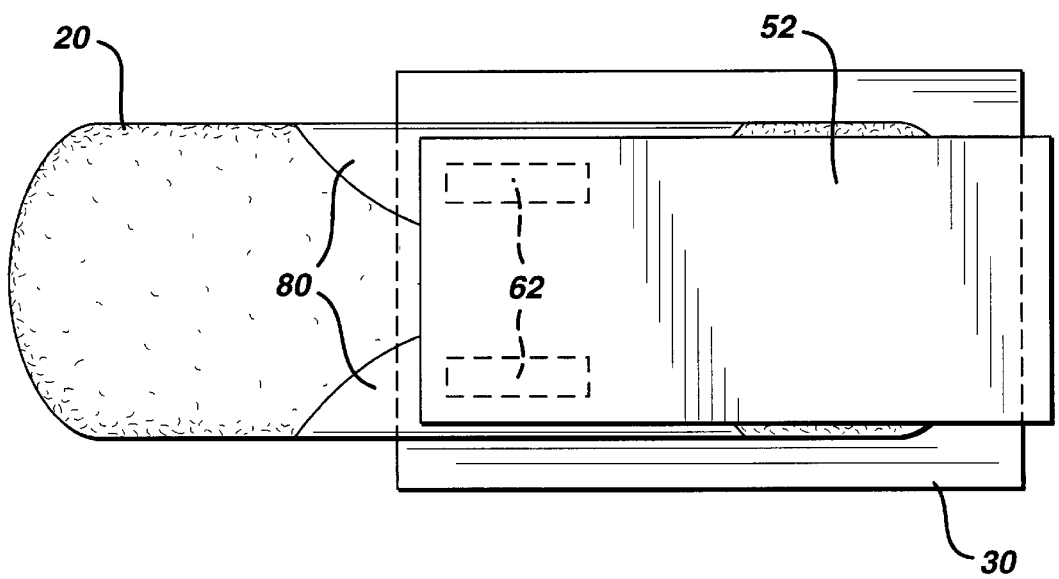
FIG. 11 depicts a napkin wherein the release liner extends beyond the napkin such that it also acts as an opening element for the prepackaged article.

FIG. 11 is a top view of the sanitary napkin 20 in which the release liner 52 extends beyond the perimeter of the wrapper 30. As depicted previously, the wing positioning adhesive 62 on the wings 80 is protected by release liner 52. This embodiment is highly desirable in that the release liner 52 can be used as an opening tab, while also protecting the wing positioning adhesive.

Figure 12:
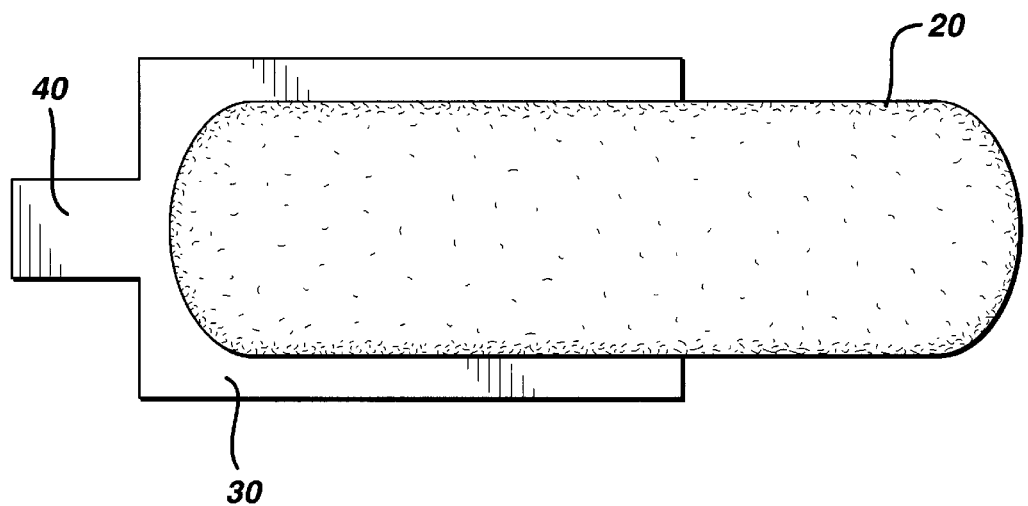
FIG. 12 depicts the tab used for opening the wrapper and gaining access to the napkin being incorporated in the wrapper.

FIG. 12 is a top view of a sanitary napkin 20, in which the tab 40 is used for opening the wrapper is integrally formed within the wrapper 30. The concept of incorporating the tab as part of the wrapper is disclosed in U.S. Pat. Nos. 5,088,993 and 4,917,675, hereby incorporated by reference.

Sanitary napkins are commercially available in multiple sizes and shapes, and can vary according to individual needs. Without limitation, the common names for the variety of externally worn sanitary napkin products include pantyliners, full-size pads, and ultrathins. The majority of sanitary napkins are either rectangular or hour-glass shaped to fit in the crotch of undergarments. Most products are attached directly to a user's undergarment, and contact the perineum intimately when the undergarments are pulled up. Alternatively, sanitary napkins can be attached directly to the body with body adhering adhesives, or held in place against the body from pressures exerted by the labia. U.S. Pat. No. 5,658,270 discloses body adhering sanitary protection products, herein incorporated by reference.

Many of the incremental changes that have evolved in the development of new sanitary napkins are targeted to improve protection of the products. Compressive forces acting on the pads from body position and activity, can distort the pad in proximity of the vaginal opening, resulting in a limited area for the fluid to contact the product when exiting the vaginal opening. Therefore, lateral extensions, commonly referred to as wings, accompany many products in an effort to reduce leakage that can occur due to the reduced area or channeling from the distortion. The lateral extensions also act to keep the sanitary napkin in the location it was originally placed. Lateral extensions can be both flexible and stiff, can contain adhesive or not, can be wrapped around the underside of undergarments, can attach to the underside of undergarments, or can be held against or attached to the body. Sanitary napkins typically contain two lateral extensions, but one of ordinary skill in the art would readily appreciate that more than two lateral extensions could be used to enhance a product's performance.

Sanitary napkins are typically made from a number of separate elements. A simplistic configuration would include the following elements: a liquid permeable cover material representing the body-contacting surface, a liquid impermeable material representing a backsheet as the opposite surface, and an absorbent material or combination of absorbent materials contained between the two surface defining materials. Adhesives can be added, and made operable with or without the presence of heat and pressure, to adhere the separate elements to one another. Adhesives can also be applied to the outer surfaces of the product for either attaching to undergarments, or directly to the body. A transfer layer or material may optionally be placed between the liquid permeable material and the absorbent material to improve the transfer of fluid into the absorbent materials. The foregoing statements are intended to describe the basic elements contained within the majority of sanitary napkins commercially available; however, the present invention is not limited to disposable absorbent articles comprising the disclosed elements. The art is replete with many additional technologies aimed towards improving the performance and comfort of sanitary napkins, all of which would not alter the utility of the present invention.

The liquid permeable cover material may be a nonwoven fabric such as a spunbonded fabric, a thermal bonded fabric, a resin bonded fabric, and the like; an apertured polymeric films such as DRI-WEAVE, and the like; or any other suitable covering material that is capable of allowing fluid to permeate and be comfortably worn against the perineum.

After discharged fluid contacts the cover of the sanitary napkin, the fluid is transferred from the cover material to the absorbent materials for storage. This can include the use of an additional transfer layer to facilitate the kinetics of this step. A representative, non-limiting list of materials useful as the absorbent includes cellulosic fibers, such as wood pulp and cotton pulp; synthetic fibers, such as polyesters and polyolefins; superabsorbent polymers, such as polyacrylic acid, and the like. Preferably, the structure includes wood pulp and about 5 to 80% fusible, thermoplastic fibers.

To prevent any absorbed fluid from leaking out of the bottom of the napkin and onto the body or clothing, a liquid impermeable material is added as a backsheet. Useful backsheet materials include, without limitation, polymeric films or coatings, such as polyolefins (e.g., polyethylene and polypropylene), polyvinyls (e.g., polyvinyl acetate, polyvinyl chloride, and poyvinylidene chloride), copolymers (e.g., ethylene vinyl acetate), and blends or laminates of one or more of the above polymers; bodily fluid repellant structures such as nonwovens, apertured films, and repellant fiber layers integrated into the bottom layer of the absorbent materials. Preferred backsheet materials include polypropylene films and bodily fluid repellant nonwovens. The most preferred barrier is constructed out of polypropylene films Adhesives are often times included in the construction of sanitary napkins to adhere the multiple elements described above. Positioning adhesive can also be applied to the impermeable barrier material, allowing the sanitary napkin to be attached to the crotch of undergarments. To eliminate gaps between the body and the sanitary napkin, there has also been innovations disclosing methods of using adhesives on portions of the liquid permeable surface for attaching the napkins directly to the perineum. A representative, non-limiting list of materials useful as either construction or positioning adhesives includes acrylics, starch based hot melts, adhesives based on block copolymers of vinyl aromatic hydrocarbon and one or more conjugated diene or hydrogenated aliphatic blocks, polylactic acids, hot melts based polyolefins such as amorphous poly-alphaolefins which may consist of one or more of the following monomers: propylene, ethylene, butene, and hexene; hot melts based on low density polyethylene or low density polyethylene copolymers including ethylene vinyl acetate, methyl acrylate, n-butyl acrylate, and acrylic acid. Typical positioning adhesives that are well known in the art are based styrenic block copolymers as disclosed in U.S. Pat. Nos. 5,149,741; 5,143,968; and 5,057,571.

The wrapper is understood to be made from any and all materials that wrap the sanitary napkin, thereby protecting it adequately from external contact before it is used, and which also can be used to wrap and dispose of the used product. For example, the wrapper can be made from paper, non-fabric, polymeric films, fibrous nonwovens, rubber, a combination of one or more of these materials or of other appropriate materials. Preferably, it is made from a thin plastic film which is liquid impermeable, such as polyethylene, polypropylene and the like of which polyethylene is most preferred.

The absorbent article is in direct contact with the wrapper, is understood to mean that the sanitary napkin and the wrapper are coextensive with each other to the percentages set forth above. This contact, nonetheless, may be indirect, that is, there may be an additional material between the absorbent article and the wrapper. Typically, when dealing with a sanitary napkin, a sheet of release liner can be used between backsheet of the sanitary napkin and the wrapper, the first surface of that release liner is used to protect the adhesive strip applied to the backsheet of the sanitary napkin, and the second surface opposite this sheet is preferably fixed in such a way that it will not come loose from the wrapper.

Also in accordance with the terms used herein, releasably attached means that the substratum in fixed to another until some small mechanical constraint created by the user will separate them, without considerable harm to any of the surfaces involved. Preferably, an adhesive of permanent touch is used, also called a pressure sensitive adhesive (or PSA), known to those in the art, for joining together the wrapper to the sanitary napkin, etc.

As used herein, a tab that moves towards the transverse border closest to the aforementioned wrapper, means that a transverse border of the sanitary napkin (sanitary napkin) has an extension or an appendix to it, which moves beyond the sanitary napkin, preferably longitudinally, and which can extend up to the transverse border closest to the wrapper, and which may be shorter or longer than the wrapper. The role of this tab is for the user to pull it and thus unwrap or break open the wrapper, separating it from the sanitary napkin.

The tab of the transverse border of the sanitary napkin, in the case in which the invention is represented by the sanitary napkin, may be an extension fixed to any of the components of the structure. That is, if the components of the structure of the sanitary napkin are overlaid layers including a covering, for example, a non-fabric, a panel of absorbent material such as wood pulp and a layer of lining, such as a thin polypropylene film, any of these materials or more than one may be extended, or have an appendix, thus making up the tab which will allow the user to grasp something when opening the prewrapped product.

The tab of the transverse edge of the sanitary napkin can be made from any appropriate material, for example, paper, non-fabric, etc. It may also have any appropriate configuration, for example a strip, a string, a loop, etc. Alternatively the tab can be manufactured or incorporated as part of the napkin, not added as a separate item. The tab can be incorporated as a die cut part of the napkin.

Optionally, the prewrapped sanitary napkin used in this invention may also have a second additional tab, in the transversal border opposite the one already described. This makes it possible, once the protective wrapper has been torn open and the sanitary napkin separated from the wrapper, for the user to have available two different tabs to grasp the sanitary napkin, allowing for greater ease in the handling and greater hygiene at the moment of putting the product to use.

The present invention also contemplates the opening for the prewrapped good described, characterized by the fact of pulling a transverse tab of the sanitary napkin and the transverse edge of the wrapper in opposite directions.

The present invention also includes methods for making the prewrapped articles described herein. The present invention comprises a method for providing a prewrapped article comprising:

providing a sanitary napkin having opposing top and bottom surfaces said sanitary napkin having distal and proximal ends, and first and second longitudinal edges extending therebetween;

providing a wrapper having opposing top and bottom surfaces, said wrapper having distal and proximal ends and first and second longitudinal edges extending therebetween, said longitudinal edges of said wrapper are shorter than said longitudinal edges of said sanitary napkin, said top surface of said wrapper coextensive with less than about half of said bottom surface of said sanitary napkin, such that said longitudinal edges of said wrapper extends beyond said longitudinal edges of said sanitary napkin;

wherein said distal end of said sanitary napkin is folded at least once, substantially 180 degrees towards said top surface of said sanitary napkin along a first fold axis substantially perpendicular to said longitudinal edges of said sanitary napkin, said first fold axis is proximal to said distal end of said wrapper.

In a further preferred embodiment of the invention sanitary napkin and said wrapper are folded substantially 180 degrees towards said top surface of said sanitary napkin along a second fold axis, substantially parallel to said first fold axis, said second fold is proximal to said first fold axis. The sanitary napkin and wrapper are then sealed by suitable means along the perimeter of the package formed by the wrapper and the sanitary napkin. The perimeter is understood to be the area within 2.5 centimeters, preferably within 1 centimeter of the exterior edges and most preferably within 0.5 centimeters of the exterior edges of the wrapper.

The invention has been illustrated by, but is not intended to be limited to, the above description and examples. The scope of the invention is to determined by the claims attached hereto.

What is claimed is:

1. A disposable article comprising;
   a. a pad having opposing top and bottom surfaces, said pad having distal and proximal ends, and first and second longitudinal edges extending therebetween; and
   b. a wrapper having opposing top and bottom surfaces, said wrapper having distal and proximal ends that are proximal the distal and proximal ends, respectively, of said pad, and first and second longitudinal edges extending therebetween, wherein said longitudinal edges of said wrapper are shorter than said longitudinal edges of said pad, and said top surface of said wrapper is coextensive with greater than about half, but less than all, of said bottom surface of said pad, such that said longitudinal edges of said wrapper extend beyond said longitudinal edges of said pad at said distal ends.

2. The disposable article of claim 1 wherein said pad further includes a tab attached to its proximal end.

3. The disposable article of claim 2 wherein said distal end of said pad is folded at least once, substantially 180 degrees towards said top surface of said pad along a first fold axis substantially perpendicular to said longitudinal edges of said pad, said first fold axis being proximal to said distal end of said wrapper.

4. The disposable article of claim 3 wherein said pad and said wrapper are folded substantially 180 degrees towards said top surface of said pad along a second fold axis, substantially parallel to said first fold axis, said second fold being proximal to said first fold axis.

5. The disposable article of claim 1 wherein said pad further includes first and second wings attached to and extending beyond said first and second longitudinal edges of said pad.

6. The disposable article of claim 5 wherein said first and second wings are folded substantially 180 degrees towards said top surface of said pad along fold axes which are parallel and adjacent to said first and second longitudinal edges of said pad.

7. The disposable article of claim 6 wherein said distal end of said pad is folded at least once, substantially 180 degrees towards said top surface of said pad along a first fold axis substantially perpendicular to said longitudinal edges of said pad, said first fold axis being proximal to said distal end of said wrapper.

8. The disposable article of claim 7 wherein said pad and said wrapper are folded substantially 180 degrees towards said top surface of said pad along a second fold axis, substantially parallel to said first fold axis, said second fold being proximal to said first fold axis.

9. The disposable article of claim 1 further including a release liner in between said pad and said wrapper.

10. The disposable article of claim 9 wherein said release liner is securely attached to said wrapper and releasably attached to said pad.

11. The disposable article of claim 1 further including a release liner releasably attached to the bottom surface of said pad, and extending over the distal end of said pad covering a portion of the top surface of said pad.

12. The disposable article of claim 11 wherein the portion of release liner attached to the bottom surface of said pad is securely attached to said wrapper.

13. A method for preparing a prewrapped disposable article comprising:
   a. providing a pad having opposing top and bottom surfaces, said pad having distal and proximal ends, and first and second longitudinal edges extending therebetween;
   b. wrapping said pad in a wrapper having opposing top and bottom surfaces, said wrapper having distal and proximal ends that are proximal the distal and proximal ends, respectively, of said pad, and first and second longitudinal edges extending therebetween, wherein said longitudinal edges of said wrapper are shorter than said longitudinal edges of said pad, and said top surface of said wrapper is coextensive with greater than about half, but less than all, of said bottom surface of said pad, such that said longitudinal edges of said wrapper extend beyond said longitudinal edges of said pad at said distal ends;
   c. wherein said distal end of said pad is folded at least once, substantially 180 degrees towards said top surface of said pad along a first fold axis substantially perpendicular to said longitudinal edges of said pad, said first fold axis being proximal to said distal end of said wrapper.

14. The method of claim 13 wherein the perimeter of the wrapper and napkin is sealed by forming perforations.

15. The method of claim 13 wherein the perimeter of the wrapper and napkin is sealed by applying adhesive.

* * * * *